United States Patent [19]

Thang et al.

[11] 4,039,382

[45] Aug. 2, 1977

[54] IMMOBILIZED RIBONUCLEASE AND ALKALINE PHOSPHATASE

[75] Inventors: Minh-Nguy Thang, Bagneux; Annie Guissani born Trachtenberg, Fresnes, both of France

[73] Assignee: Choay S. A., Paris, France

[21] Appl. No.: 678,459

[22] Filed: Apr. 19, 1976

[30] Foreign Application Priority Data

Apr. 23, 1975 France ............................. 75.12667

[51] Int. Cl.$^2$ ........................... C07G 7/02; C12B 1/00
[52] U.S. Cl. .................................. 195/28 N; 195/63; 195/68; 195/DIG. 11; 195/116
[58] Field of Search .................. 195/63, 68, DIG. 11, 195/116, 28 N

[56] References Cited

PUBLICATIONS

Lee, J. C., Preparation and Properties of Water Insoluble Derivatives of Ribonuclease Ti. Biochim. Biophys. Acta., vol. 235, 1971, (pp. 435–441).
Woetall, H. H., Alkaline Phosphatase Insolubilized by Covalent Linkage to Porons Glass., Nature., vol. 223, 1969, (pp. 959–960).
Hultin, H. O., Characteristics of Immobilized Multi-Enzyme Systems, Journal of Food Science, vol. 39, 1974, (pp. 647–652).
Zaborsky, O., Immobilized Enzymes, CRC Press, Cleveland, Ohio, 1973, (pp. 124–126).

Primary Examiner—David M. Naff
Attorney, Agent, or Firm—Browdy and Neimark

[57] ABSTRACT

An insoluble, solid matrix carrying simultaneously several different enzymatic functions, is constituted by the conjoint association by irreversible binding on a previously activated matrix support, of a nuclease selected from the group of ribonucleases A, $T_1$, $T_2$, $U_2$ and an alkaline phosphatease. Free activated groups of the matrix after binding of the enzymes, are neutralized by a free amino organic base. The support is selected from among non-denaturing supports effecting the irreversible physical adsorption of the enzymes, such as supports of glass or quartz beads, highly cross-linked gels of the agarose or cellulose type. Polymers $A_nU_{OH}$, $A_n\text{-}C_{OH}$, $A_nG_{OH}$ and/or oligonucleotides U, C, A or G, of predetermined lengths, can be obtained by fractionating the polyribonucleotides by incubation with the insoluble solid matrix.

16 Claims, No Drawings

IMMOBILIZED RIBONUCLEASE AND ALKALINE PHOSPHATASE

BACKGROUND OF THE INVENTION

1. Field of the Invention

The present invention relates to matrices carrying simultaneously several different enzymatic functions and more particularly to complexes constituted by enzymes bound irreversibly on insoluble supports, as well as to the process for the preparation of these matrices. The present invention also relates to a process for the preparation, by means of said matrices, of oligonucleotides and polynucleotides with specific end groups.

2. Description of the Prior Art

It is known to fractionate polyribonucleotides by action of enzymes, to obtain various polynucleotides and oligonucleotides, and notably oligo U (or uridine-oligonucleotides) and oligo G (or guanosine-oligonucleotides). These enzymatic actions comprise essentially two stages, of which the first consists of subjecting the polyribonucleotides used to enzymatic hydrolysis by using either the ribonuclease of sheep's kidney [K. KASAI and M. GRUNBERG-MANAGO : Eur. J. Biochem. I (1967), 152], or beef pancreatic ribonuclease [G. SCHMIDT — The nucleic Acids I (1955), p.555, Chargaff and Davidson Ed.] if it is sought to obtain uridine-oligonucleotides (that is to say oligonucleotides ended by a pyrimidine group), or ribonuclease $T_1$ separated from takadiastase of *Aspergillus orizae*, if it is sought to obtain guanosine-oligonucleotides (that is to say oligonucleotides ended by a purine group) [Egami TAKAHASHI and UCHIDA - Progress in nucleic Acids and Research and Molecular Biology, XII, 1964, 59]. This enzymatic hydrolysis cleaves the polymeric chain at the 5'-phosphate junction, giving rise to a 3'-phosphate group, and it is followed by a second stage, which is a dephosphorylation by the alkaline phosphatase of *Escherichia Coli*.

The enzymes successively applied are in solution, so that it is necessary, at the end of the operations which have just been described, to separate the products obtained from the enzymes used, which are often very resistant so that these processes are difficult to apply and the yield of oligonucleotide obtained is very low.

To avoid these difficult separating processes which are complicated and expensive, it has been proposed to substitute for the enzymes in solution used in the course of the two stages of the process which has just been described, enzymes rendered insoluble by binding to a support. The work of PORATH and KRISTIANSEN ("The Proteins" vol. I, 3rd Ed., Academic Press) has, in fact, made known enzymes rendered insoluble by binding on a matrix of glass or of agarose. However, the processes proposed, which successively apply insoluble enzymes, if they resolve in part the difficulties of separation of the soluble enzymes, also however involve a considerable number of operations, so that it is still necessary, in any case, to resort to processes involving long and complicated operations, which are of little practicality on the industrial scale.

OBJECTS AND GENERAL DESCRIPTION OF THE INVENTION

Accordingly it is an object of the present invention to provide matrices carrying simultaneously several different enzymatic functions and processes for preparing them, which respond better to the requirements of practice than previously known enzymes bound individually to an insoluble support.

It is another object of the invention to provide such matrices which permit the fractionation of polyribonucleotides into copolymers or into oligonucleotides, in a single operation, under kinetic conditions which are very satisfactory and with excellent yields, by the simultaneous action of specific enzymes, which enable control of the fractionation in order to obtain specifically sought copolymers or oligonucleotides.

Other objects and advantages of the present invention will appear from the description which follows.

According to the invention there is provided a matrix carrying simultaneously several different enzymatic functions, characterized in that it is constituted by the conjoint association of a nuclease and of an alkaline phosphatase, with an insoluble solid matrix, adapted to bind the above-said enzymes irreversibly.

According to a preferred embodiment of the matrix carrying several different enzymatic functions according to the invention, the nuclease is selected from the group which comprises ribonucleases, and notably ribonucleases A, $T_1$, $T_2$, $U_2$.

According to another advantageous feature of the invention, the insoluble support on which the enzymes are bound is selected from among non-denaturing supports effecting the irreversible physical adsorption of the enzymes, such as supports of glass or quartz beads, highly cross-linked gels notably of the agarose or, in particular, of the cellulose type.

According to another feature of the matrix according to the invention, the amounts of active enzymes fixed on the support are advantageously comprised between 0.001 and 0.15% of alkaline phosphatase, and between 0.01 and 0.05% of nuclease by weight with respect to the weight of the support.

It is also an object of the present invention to provide a process for obtaining matrices carrying several different enzymatic functions, characterized in that the solid support previously activated by means of a suitable activating substance, such as cyanogen bromide, for example, is placed in contact, in a suitable buffer solution, with enzymes to be bound on said support, namely a nuclease and an alkaline phosphatase, for a time and at a temperature which are interdependent, after which the amounts of unbound enzymes are removed by washing by means of a buffer solution identical with that used for the binding, and the free activated groups of the support are neutralized by means of a free amino organic base such as lysine, arginine, ethanolamine, aniline and the like.

According to an advantageous embodiment of the process according to the present invention, the buffer solution applied is at a pH between 8.1 and 8.6.

According to another preferred embodiment of the process of the present invention, the organic base used as neutralizing agent for the free activated groups of the support after binding of the enzymes, is at a pH between 8 and 10.

According to another preferred embodiment of the process according to the invention, the duration of contact between the enzymes to be bound and the binding support is between 1 and 16 hours for temperatures comprised between 20° C and 4° C.

Another advantageous feature of the process according to the invention provides for the contacting, in a buffer solution at pH 8.1 - 8.6 of the support with amounts of enzymes comprised between 0.001 and 0.15% by weight of alkaline phosphatase and between 0.001 and 0.05% by weight of nuclease, with respect to the weight of the support.

According to the invention, the amount of active enzymes bound on the support, measured after washing and neutralization, is comprised between 43 and 85% with respect to the amount of alkaline phosphatase initially used and between 47 and 95% with respect to the amount of nuclease initially used.

According to the present invention there is also provided a process for obtaining polymers, $A_nU_{OH}, A_nC_{OH}, A_nG_{OH}$ and/or oligonucleotides U, C, A, or G, of predetermined lengths, characterized in that polyribonucleotides are fractionated by incubation with an insoluble solid matrix, which carries simultaneously several different enzymatic functions. It should be understood that throughout the present specification and claims U, C, A and G have their usual meaning, i.e., uridine, cytosin, adenine and guanosine, respectively.

According to a preferred embodiment of the process of fractionation according to the present invention, the matrix applied carries a nuclease and an alkaline phosphatase.

According to the invention, the polyribonucleotides applied are selected from the group which comprises, notably, $poly(A_mU_1)_n$, $poly(A_mC_1)_{n'}$, $poly(A_{m''}G_1)_{n''}$ when it is sought to obtain polymers $A_nU_{OH}$, $A_nO_{OH}$, and $A_nG_{OH}$, and they are selected from the group which comprises homopolynucleotides poly U, poly C, poly A and poly G or their copolymers, when it is sought to obtain oligonucleotides.

In a preferred embodiment of the process of fractionation of polynucleotides according to the invention, it is carried out continuously or semi-continuously by the passage of the polynucleotides to be fractionated, over columns containing the matrix according to the present invention.

For the application on the one hand of the process for the production of matrices carrying simultaneously several different enzymatic functions, in accordance with the foregoing features, and on the other hand of the process of fractionation of polynucleotides by means of the matrices, operations are preferably carried out under the following conditions:

I. Production of insoluble, solid matrices carrying simultaneously several different enzymatic fractions 1. Choice and treatment of the matrix As the solid matrix either treated glass beads are used, or cellulose or agarose gel, activated according to the method of Axen, Porath and Ernback ["NATURE", 214, (1967) 1302] then proceeding as follows: the cellulose or agarose (for example, that sold under the trademark "SEPHAROSE") is first washed over sintered glass with distilled water. To it is added water and a fresh 2% solution of cyanogen bromide (BrCN) so as to obtain a final concentration of 1.5% in BrCN, or 50 mg of BrCN, per gram of dried matrix. It is stirred at 4° C keeping the pH at 11 by the gradual addition of 4N NaOH (the operation lasts about 10 minutes), then filtered over sintered glass by effecting 3 washings with a total of 10 volumes of sodium bicarbonate.

For immediate use, it is rinsed 5 to 6 additional times with bicarbonate.

For later use, the activation not being very stable when the cellulose or agarose are in suspension, the latter is washed by mixtures of water richer and richer in acetone, then the paste obtained is dried in the desiccator. Just before use, it is washed carefully with sodium bicarbonate in order to remove all traces of acetone.

2. Binding of the enzymes

Binding of the enzyme is then carried out on the treated matrix, by proceeding as described below.

The enzymes to be bound on the matrix are selected respectively from among nucleases, on the one hand, and from among alkaline phosphatases on the other hand. The alkaline phosphatases utilized can be of vegetable or animal origin, but alkaline phosphatases of bacterial origin are preferred and notably alkaline phosphatase from Escherichia Coli, on account of its particularly high activity.

Among the nucleases, the choice may be directed, preferably, to the ribonucleases, and notably to the ribonucleases A, $T_1$, $T_2$, $U_2$.

The activity of the enzymes used is measured previously and is checked in the course of the production process, by the following methods:

Activity of the ribonucleases

Activity of pancreatic ribonuclease

It is measured by following the degradation of the poly U: 1 Unit = 1 O.D. (optical density) of poly U, freed in one minute at 37° C into the acidosoluble supernatant liquid.

Activity of the $T_1$ ribonuclease

It breaks the guanosine bond specifically thereby giving oligonucleotides ended by G-3'-P.

Its activity was measured by titrating the degradation of the t-ARN of E. Coli. in the presence of EDTA.

0.1 unit represents 1 O.D. freed in 15 minutes at 37° C. in the acidosoluble supernatant liquid.

Activity of the alkaline phosphatase

The transformation of the para-nitro-phenylphosphate into para-nitrophenol absorbing at 340 mn is followed by the spectrophotometer. One unit = 1 O.D. of para-nitrophenol freed in one minute at ambient temperature.

To bind the enzymes on the treated matrix, a mixture of the said matrix is stirred with phosphatase and nuclease, for a predetermined time and temperature, in a buffer solution, at pH 8.1 to 8.6, preferably in 0.02 M Tris buffer at pH 8.3.

To remove the unbound enzymes, it is washed on a filter several times by means of the same buffer solution as above, then the mixture is resuspended in the same buffer.

The free groups which remain on the activated matrix are then saturated by means of an amino organic base, at a pH comprised between 8 and 10. Among the amino organic bases which may be applied in the process according to the present invention, may be mentioned, by way of non-limiting examples, lysine, arginine, ethanolamine and, preferably, aniline, used in 0.1 M solution preferably in a buffer solution such as 0.1 M Tris at pH 8.1 - 8.6. This process of neutralization of the free groups, by saturation, is followed for 3 to 20 hours at temperatures comprised between 4° C and 22° C, after which the excess organic base is removed by repeated filtrations and washings by means of the aforesaid buffer, and the paste obtained is resuspended in a buffer solution such as, for example, 0.02 M Tris buffer at pH 8.3.

It should be mentioned that the entire amounts of enzymes utilized are not bound, in all cases, on the previously treated matrix, and that the activity of the enzyme actually bound does not coincide in all cases with the amount of enzyme bound on the matrix.

Thus, as to the enzymes bound on a matrix of activated cellulose, as described in Example 1 hereunder, 92.5% of the alkaline phosphatase applied is bound to the cellulose, but measurement of the activity of the bound enzyme shows that it is 70% of the whole of the enzyme used. Similarly, the ribonuclease actually bound on the cellulose only represents 66% of the enzyme applied, and the enzymatic activity of the bound enzyme only constitutes 47% of the total activity of the ribonuclease used.

The binding of an alkaline phosphatase and of $T_1$ ribonuclease on an agarose support, as described in Example 2 below, results in a bifunctional matrix in which 85% of the phosphatase applied and 94% of the ribonuclease $T_1$ applied, are bound, and of which the enzymatic activity of the phosphatase corresponds to 65% of that of the bound enzyme, whilst it is expressed entirely for the ribonuclease $T_1$, that is to say that it is, for the latter, 94% with respect to the enzyme initially used.

The enzymes bound on a solid matrix, according to the present invention are better protected, with respect to inactivation, than soluble enzymes and are hence more stable. The binding of the enzymes on the matrix is practically irreversible since the bifunctional matrix according to the present invention is utilizable a very large number of times without loss of activity and without releasing enzymes into the medium.

The amounts of phosphatase and of nuclease bound are not critical and are selected so that the phosphatase is in excess for the calculated time of incubation for nuclease: in fact, an excess of phosphatase is not troublesome and permits, on the contrary, complete dephosphorylization to be ensured, although the presence of an excess of nuclease would involve a more extensive fractionation of the polynucleotides than that sought according to the invention.

Proportions comprised between 0.001 and 0.15% of alkaline phosphatase and between 0.001 and 0.05% of nuclease by weight with respect to the weight of the support, are given by way of indication, but are not critical in character.

II. Preparation of copolymers $A_nU_{OH}$, $A_nC_{OH}$, or $A_nG_{OH}$, the and oligonucleotides U, C, A or G A. To obtain copolymers $A_nU_{OH}$, $A_nC_{OH}$ or $A_nG_{OH}$, the procedure is as follows:

1. The synthesis of polyribonucleotides of the formula $(A_mU_1)_n$, $(A_{m'}C_1)_n$, or $(A_{m''}G_1)_{n''}$ is carried out in known manner from ADP, UDP, CDP and GDP in the presence of polynucleotide-phosphorylase.

2. The polymer of formula $(A_mU_1)_n$, $(A_{m\text{-}207}C_1)_n$, or $(A_{m''}G_1)_{n''}$ obtained in the course of the first stage is subjected to the action of the bifunctional matrix according to the present invention, which degrades it into a polymer of the formula $A_nU\text{-}P$, $A_nC\text{-}P$ or $A_nG\text{-}P$ under the action of a ribonuclease, and causes the dephosphorylation of said polymer into $A_nU_{OH}$, $A_nC_{OH}$ or $A_nG_{OH}$ by the action of alkaline phosphatase. It should be noted that the alkaline phosphatase only exerts its action on the terminal phosphate group, so that the presence of an excess of phosphatase is without importance, contrary to what occurs with ribonuclease whose degradation effect is capable of continuing to the monomer, that is to say beyond the desired degradations, if it is present in excess.

The characterization of the polymer obtained is effected:
a. by chromatography on 3MM Whatman paper By measuring the radioactivity, no contamination of the polymer is detected.

b. by phosphorolysis with polynucleotide-phosphorylases of E. Coli and C. perfringens The production of 100% phosphorolysis with these two enzymes indicates the absence of phosphate at the 3' end of the polymers c. by alkaline hydrolysis After hydrolysis for 18 hours with 0.3M potash, followed by chromatography on DEAE-cellulose (diethylaminoethylcellulose) paper, in the presence of 0.065 M sodium bicarbonate or on a PEI plate (polyethyleneimine) in the presence of 1N acetic acid, then 0.3M LiCl, all of the radioactivity in the form of uridine is recovered, which indicates simultaneously an absence of internal uridine and an absence of terminal phosphate (hence an additional effect of the alkaline phosphatase).

B. To obtain oligonucleotides U, C, A or G. As starting substrates, for the preparation of oligonucleotides, the homopolynucleotides poly U, poly C, poly A and poly G, or their copolymers, are used on which the bifunctional matrix according to the present invention is caused to act. The action of the matrix is stopped when 25 or 50% degradation (measured by the optical density of the acidosoluble supernatant liquid) are obtained. The matrix is removed by centrifugation. A mixture of oligonucleotides is obtained which are separated by passage over an anionic exchange column, notably DEAE-cellulose or DEAE-Sephadex, in the presence of 7M urea. Elution may be effected by a saline gradient (sodium chloride or sodium bicarbonate, triethylammonium acetate).

For the oligonucleotides which are relatively unstructured and do not aggregate, such as oligo U, it is easy to separate the oligonucleotides of size less than or equal to 9 by filtration over a "SEPHADEX C25" column in an 0.15 M ammonium bicarbonate buffer.

To obtain a satisfactory separation, it is advantageous to bind the substances to be separated on the upper part of the column, corresponding to 10% of the useful volume.

Characterization of the oligonucleotides:

1. by chromatography
   a. For identification of the oligonucleotides, use is made of 3MM Whatman paper, and, as solvent, concentrated n-propanol-ammonia-water (55/10/35,V/V) [KASAI, 1967]. Filtration on molecular sieves can also be used, elution being carried out in the presence of 8M urea and of 0.5M ammonium bicarbonate.
   b. By thin layer chromatography on a PEI plate. In order to ascertain the nucleoside composition and the nucleoside-monophosphate composition after alkaline hydrolysis, the technique used is that of E. and K. Randerath [Anal. Biochem. 12 (1965) 83] which consists of allowing N acetic acid to migrate up to 4 cm from the origin, and then replacing it by a 0.3M LiCl.

After locating the stains by UV, by means of carriers previously mixed with the hydrolysate, they are defined, the corresponding stain is scraped, and then the radioactivity fixed is counted in a scintillation counter.

2. By phosphorolysis

In order to check whether the dephosphorylation is complete, the oligonucleotides obtained are subjected to phosphorolysis by polynucleotide-phosphorylase of E. Coli. The following results were obtained:

a. On 25% degradation (measured in the acidosoluble substrate) of the polymer used as substrate, Whatman chromatography shows that some substrate remains, that is to say polymer or oligonucleotides longer than $8n$ and that there are no very short oligonucleotides, that is to say shorter than or equal to $3n$; it is particularly oligonucleotides of size larger than or equal to $6n$ that are found. Phophorolysis of these oligonucleotides indicates on the one hand that they do not have phosphate at their 3'end, and on the other hand, that they are free of very short oligonucleotides (since, as is known, oligonucleotides must be longer than $2n$ to be able to undergo phosphorolysis)

b. At 50% degradation of the polymers used as substrates, Whatman paper chromatography shows on the other hand, a preponderance of short oligonucleotides, confirmed by phosphorolysis, which is also compatible with the absence of phosphate and the 3' end.

3. Study of the length of the oligonucleotides

The average length of the oligonucleotides has been studied in the acidosoluble supernatant liquid as a function of the incubation time. Aliquot fractions of the acidosoluble supernatant liquid were withdrawn at the following times : 0–2–16–26–33–49–51 hours, the total duration of incubation being 51 hours, and were precipitated in an acid medium, then neutralized to undergo alkaline hydrolysis. Alkaline hydrolysis with a final concentration of 0.3M KOH was then carried out for 18 hours at 37° C, then for 1 hour at 50° C (to remove the cyclic esters possibly formed during the hydrolysis with ribonuclease $T_1$).

Chromatography of the hydrolysates on a PEI plate then followed, to obtain the proportion of GMP and of G in each of them. The hydrolysis was checked by measuring the optical density and the radioactivity of the acidosoluble supernatant liquid, the last time of incubation (51 hours) corresponding to 50% degradation.

the length of the oligonucleotide, namely $n + 1$, is equal to :

(GMP/G)+ 1 which signifies that a constant ratio GMP/G results in a constant average length of the oligonucleotides. It should be mentioned that the affinity of the nucleases for the polymers is much greater than for the oligonucleotides, so that as long as there are polymers in a medium, the latter are preferentially degraded, which explains to a certain extent the constancy of the average length of the oligonucleotides in the acidosoluble supernatant liquid, which will be apparent from the following table:

| Control time (in hours) | GMP | G | GMP/G |
| --- | --- | --- | --- |
| 0 | 1932 | 351 | 2.7 |
| 16 | 15656 | 2286 | 6.85 |
| 26 | 17872 | 2879 | 6.25 |
| 33 | 31411 | 5635 | 5.6 |
| 49 | 38125 | 4876 | 7.85 |
| 51 | 30519 | 4403 | 6.95 |

It should be stressed that the controls carried out showed that there is practically no loss of the material initially utilized.

In addition to the foregoing features, the invention comprises other features which will emerge from the description which follows.

The invention relates more particularly to matrices which carry simultaneously several different enzymatic functions and to their process of production, to the processes for the preparation of oligonucleotides and of polynucleotides with specific end groups, utilizing said matrices, as well as the means adapted to the application of these processes and to the production of said matrices, and to the polynucleotides and oligonucleotides obtained by applying the above-said processes.

The invention will be better understood by means of the further description which follows, with reference to examples of carrying out of the processes according to the present invention. It must however be well understood that these examples are given solely by way of illustration of the invention and that they are not to be considered as constituting any limitation thereof.

EXAMPLES

EXAMPLE 1

Production of a matrix according to the invention by binding of alkaline phosphatase and ribonuclease on cellulose 1. Activation of the support The cellulose is washed on sintered glass with distilled water, then water and a fresh 2% solution of cyanogen bromide (BrCN) are added so as to obtain a final concentration of 1.5% of BrCN, namely 50 mg of BrCN per gram of dry cellulose. It is stirred at 4° C whilst maintaining the pH at 11 by gradual addition of 4N NaOH (the operation lasting about 10 minutes), then it is filtered on sintered glass, with washing 3 times with a total of 10 volumes of sodium bicarbonate.

For immediate use, it is rinsed an additional 5 to 6 times with sodium bicarbonate.

For later use, the washings are done with water mixtures richer and richer in acetone, then the paste obtained is dried in a dessicator. Just before use, it is washed carefully with sodium bicarbonate in order to remove all traces of acetone.

2. Binding of the enzymes

A solution containing 2.5 ml of activated cellulose (representing about 0.4g of dry cellulose), 350 μg of alkaline phosphatase, representing 100 units and 40 μg of beef pancreatic ribonuclease, representing 80 units, in a 0.02M Tris buffer at pH 8.3, is stirred gently for 16 hours at 4° C.

The unbound enzymes are removed by carrying out 5 successive washings followed by filtrations, in 5 times 5 ml of 0.02M Tris buffer, pH 8.3, then it is resuspended in the same buffer.

The amount of enzymes bound is 92.5 units on 100 of alkaline phosphatase and 53 units on 80 ribonuclease, namely 92.5% and 66% respectively, binding yield.

The remaining free groups on the cellulose are then saturated, by addition of 0.1 M aniline in 0.1 M Tris buffer, pH 8.3, followed by stirring for 16 hours at 4° C.

The unbound aniline is then removed by carrying out 5 successive washings followed by filtrations, in 5 times 5 ml of 0.1M Tris buffer, pH 8.3.

The enzymes bound on the cellulose are then resuspended in 0.02M Tris buffer, pH 8.3, and then the activity of the bound enzymes is measured by titration of the suspension and of the filtrate; there are thus found:

Alkaline phosphatase: 40 units in suspension and 25 units in the filtrate, namely a final yield of 43% of active bound enzyme.

Beef pancreas ribonuclease: 25 units in the suspension and 16 units in the filtrate, namely a final yield of 47% active bound enzyme.

EXAMPLE 2

Production of a matrix according to the invention, by binding alkaline phosphatase and ribonuclease $T_1$ on an agarose support 1. Activation of the support The procedure is as described in Example 1 activating cellulose, using as the support agarose beads marketed under the name "SEPHAROSE 4B".

2. Binding of the enzymes 1 g of activated "SEPHAROSE 4B" with on the one hand 29 units, namely 54 μg, of alkaline phosphatase and on the other hand 7000 units, namely 50.2 μg, of ribonuclease $T_1$, are stirred for 16 hours at 4° C, then the procedure is as described in Example 1.

85% of the alkaline phosphatase is bound, namely 17 units, of which 11 are expressed, equivalent to an efficiency of 65% with respect to the bound enzyme, and 94% of the ribonuclease, namely 6600 units, of which the totality is expressed, equivalent to an efficiency of 94%.

EXAMPLE 3

Use of bifunctional matrices according to the invention for obtaining a polymer of formula $A_nC_{OH}$ 1st stage: Preparation of the polymer poly$(A_nC_l)_x$ by the action of polynucleotide-phosphorylase of E. Coli.

The following incubation mixture is prepared: Tris 100 mM, NaCl 18.75 mM, ADP 62.5 mM, CDP 0.62 mM (and if necessary 20 microcuries of CDP $^{14}$C labelled at α or uniformly to allow the production of a radioactive copolymer whose characteristics can easily be tested and which is available as an experimental material), polyribonucleotide-phosphorylase bound 35 polymerization units, the whole in 2.6 ml.

The incubation is carried out at 45° C. The degree of polymerization is followed by means of the percentage of phosphate freed and the reaction is stopped when the latter reaches 50% (8 hours of incubation).

A poly$(A_{100}C_1)_x$ is thus prepared.

Centrifugation is carried out to separate the polymer from the insoluble enzyme. Separation of the polymer and of the unused nucleosides-diphosphates is effected by chromatography of the preceding mixture on a column of "SEPHADEX G50" (1.2 × 11) balanced with a 0.02M Tris - 0.1M NaCl buffer, and eluted with the same buffer. 600 O.D. of polymer in 5 ml are recovered at this stage.

2nd stage: Preparation of the polymer $A_nC_{OH}$.

The foregoing polymer, namely 600 O.D., is subjected to stirring for 10 hours at 37° C in the presence of 2 units of insoluble pancreatic ribonuclease and 10 units of insoluble alkaline phosphatase, bound on the same support and in the presence of 0.2M KCl (the latter to avoid accidental bond-breakings by the ribonuclease after the A [Beers Journ.Biol.Chem.235 (1960) 2393]. 520 O.D. are recovered in the supernatant liquid. To eliminate the oligonucleotides produced by the action of the ribonuclease, the foregoing supernatant liquid is chromatographed on a column of "SEPHADEX G50" (0.9 × 40), the elution being carried out with 0.02M Tris - 0.1M NaCl buffer. 350 O.D. of copolymer are then recovered. The characteristics of the $A_nC_{OH}$ copolymer obtained are checked as described above.

EXAMPLE 4

Use of bifunctional matrices according to the invention for preparing a polymer of the formula $A_nU_{OH}$ The incubation mixture is as follows: 100 mM Tris, NaCl 18.75 mM, ADP 62.5 mM, UDP 1.3 mM (and if necessary 20 microcuries of UDP $^{14}$C labelled at α or uniformly), polyribonucleotide-phosphorylase bound 35 polymerization units, the whole in 2.6 ml. Incubation is carried out at 45° C. The remainder of the operations, as well as the controls, are carried out under the same conditions as for preparing polymer $A_{100}C_1$.

Result of the controls : the latter are satisfactory : homogeneity of the copolymer, 100% phosphorolysis, absence of internal uridine and of terminal phosphate.

EXAMPLE 5

Use of matrices according to the invention for obtaining U oligonucleotides

50 O.D. of poly-U are incubated in 100 mM Tris buffer, pH 8.3, containing 10 mM of $MgCl_2$, with an activated cellulose suspension containing 0.4 units of bound ribonuclease and 1.3 units of bound alkaline phosphatase. The incubation is stopped when the degradation has reached 25%, then 50% (measured by the optical density at 260 nm).

The suspension is then centrifuged to remove the bound enzymes on their matrix.

A mixture of oligonucleotides is obtained which are separated by passage over a column of DEAE-cellulose with an ammonium bicarbonate gradient.

The characterization of the oligo U is carried out as described above.

It is observed that there is no loss of the material initially used, calculated from the O.D. at 260 nm, which proves that there are neither nucleotides nor oligonucleotides irreversibly absorbed at any of the stages of the preparation.

EXAMPLE 6

Use of matrices according to the invention for obtaining G oligonucleotides

The incubation mixture comprises: 50 mM Tris pH 7.5, 2 mM EDTA, 4.3 O.D./ml of poly-G (if necessary 1.2 O.D. of radioactive poly-G free of contaminating traces of oligonucleotides, representing 0.2 microcurie) and 40 units of ribonuclease $T_1$ and 1 unit of alkaline phosphatase bound on activated "SEPHAROSE 4B".

A mixture of oligonucleotides is obtained which are separated by chromatography on an anion exchange column such as DEAE-SEPHADEX, in the presence of 7M urea, elution being carried out by means of sodium bicarbonate.

The characterization of the oligo G is done as described above.

It is observed that there is less than 10% loss of the material initially used, measured by radioactivity.

It is apparent from the foregoing description, that whatever the methods of operation, embodiments and applications adopted, there are thus provided matrices carrying simultaneously several different enzymatic functions and their process of production, as well as processes applying said matrices, for obtaining polynucleotides with specific end groups and oligonucleotides, which have with respect to the prior art, important advantages, amongst which should be stressed, beside the advantages which have been indicated in the foregoing, the very significant improvement in the kinetics of the process of fractionating polyribonucleotides by means of alkaline phosphatase and ribonuclease, the possibility of controlling accurately the processes of fractionation to obtain the desired substances, the excellent yields obtained and the possibility of appyling the bifunctional matrices according to the present invention to the obtaining of ARN (t-ARN, r-ARN or m-ARN) segments by selective cleavage under predetermined conditions of temperature and of ionic force.

As is apparent from the foregoing, the invention is in no way limited to those of its methods of operation, embodiments and applications which have just been explicitly described; it encompasses, on the contrary, all modifications which can occur to the technician skilled in the art without departing from the scope of the present invention.

We claim:

1. An insoluble solid matrix carrying simultaneously more than one different enzymatic function, consisting essentially of:
   an activated solid insoluble matrix support, non-denaturing for the enzymes to be attached thereto;
   a nuclease, selected from the group consisting of ribonucleases A, $T_1$, $T_2$ and $U_2$; and
   an alkaline phosphatase,
   said nuclease and said alkaline phosphatase being irreversibly bound to said matrix support, wherein the enzyme-bound matrix has no non-neutralized free activated groups thereon.

2. Matrix according to claim 1, wherein the amounts of active enzymes bound on the support are comprised between 0.315 and 47 Units of alkaline phosphatase per mg of support and between 0.001 and 0.05% of nuclease by weight with respect to the weight of the support.

3. Matrix according to claim 2, wherein the nuclease is constituted by pancreatic ribonuclease and is bound on the support in the proportion of 2 to 100 Units per mg of support.

4. Matrix according to claim 2, wherein the nuclease is constituted by the ribonuclease T, and is bound on the support in the proportion of 120 to 6000 Units per mg of support.

5. Matrix according to claim 1, wherein said non-denaturing support is selected from among glass beads, quartz beads and highly cross-linked gels of agarose or cellulose.

6. A process for obtaining the matrix of claim 1, comprising:
   contacting an activated solid insoluble matrix support, non-denaturing for the enzymes to be attached thereto, with a nuclease, selected from the group consisting of ribonucleases A, $T_1$, $T_2$ and $U_2$, and an alkaline phosphatase, in a buffer solution having an elution coefficient substantially the same as tris (hydroxymethyl) aminomethane, for a time and a temperature which are interdependent and are together sufficient to cause irreversible binding of said enzymes on said support, the pH of said buffer solution being 8.1 – 8.6; ;
   removing unbound enzymes by washing with a buffer solution identical to that used in said contacting step;
   neutralizing the remaining free activated groups of said support by means of a free amino organic base, in a pH range of 8–10; and
   removing excess organic base.

7. Process according to claim 6, wherein said solid insoluble matrix support has been activated by means of cyanogen bromide.

8. Process according to claim 6, wherein said free amino base is selected from the group consisting of lysine, arginine, ethanolamine and aniline.

9. Process according to claim 6, wherein the duration of contact between said enzymes to be bound and said support is comprised between 1 and 16 hours for temperatures comprised between 20° C and 4° C.

10. Process according to claim 6, wherein said support is contacted with amounts of enzymes allowing the binding of 0.315 Units to 45 Units by weight of alkaline phosphatase per mg of support and from 0.001 to 0.05% by weight of nuclease, with respect to the weight of the support.

11. Process according to claim 10, wherein the support is contacted with an amount of pancreatic ribonuclease allowing binding of 2 to 100 units of the latter enzyme per mg of support.

12. Process according to claim 10, wherein the support is contacted with an amount of ribonuclease $T_1$ allowing the binding of 120 to 6000 Units of the latter enzyme per mg of support.

13. Process for obtaining polymers $A_n U_{OH}$, $A_n C_{OH}$, $A_n G_{OH}$ and/or oligonucleotides U, C, A or G, of predetermined lengths, said process comprising:
   fractionating a polyribonucleotide by incubation with the insoluble solid matrix carrying simultaneously more than one different enzymatic function in accordance with claim 1.

14. Process according to claim 13, wherein said polyribonucleotide is selected from the group consisting of poly($A_m U_1)_n$, poly($A_{m'} C_1)_{n'}$, poly($A_{m'} G_1)_{n'}$, for obtaining polymers $A_n U_{OH}$, $A_n C_{OH}$, $A_n G_{OH}$, respectively.

15. Process according to claim 13, wherein said polyribonucleotide is selected from the group consisting of homo-polynucleotides poly U, poly C, poly A and poly G and their copolymers, for obtaining oligonucleotides U, C, A or G, respectively.

16. Process according to claim 13, wherein said fractionating step comprises passing said polynucleotide continuously over columns containing said matrix.

* * * * *